United States Patent [19]
Rothman

[11] Patent Number: 5,952,232
[45] Date of Patent: *Sep. 14, 1999

[54] EXPANDIBLE MICROPARTICLE INTRACELLULAR DELIVERY SYSTEM

[76] Inventor: James Edward Rothman, 402 E. 64th St., Apt. 10B, New York, N.Y. 10021

[ * ] Notice: This patent issued on a continued prosecution application filed under 37 CFR 1.53(d), and is subject to the twenty year patent term provisions of 35 U.S.C. 154(a)(2).

[21] Appl. No.: 09/156,739

[22] Filed: Sep. 17, 1998

[51] Int. Cl.$^6$ .................................................... C12N 15/64
[52] U.S. Cl. ...................... 435/459; 435/320.1; 524/560; 526/329.7
[58] Field of Search .............................. 435/172.3, 320.1; 524/560; 526/329.7

[56] References Cited

U.S. PATENT DOCUMENTS

| | | | |
|---|---|---|---|
| 5,277,914 | 1/1994 | Szoka, Jr. ................................. | 424/450 |
| 5,549,910 | 8/1996 | Szoka, Jr. ................................. | 424/450 |
| 5,567,434 | 10/1996 | Szoka, Jr. ................................. | 424/450 |
| 5,643,247 | 7/1997 | Fernandez et al. ...................... | 424/566 |
| 5,654,006 | 8/1997 | Fernandez et al. ...................... | 424/489 |
| 5,661,025 | 8/1997 | Szoka, Jr. et al. ......................... | 514/44 |

FOREIGN PATENT DOCUMENTS

| | | |
|---|---|---|
| 9319768 | 10/1993 | WIPO . |
| 9417538 | 8/1994 | WIPO . |
| 9417786 | 8/1994 | WIPO . |
| 96640265 | 12/1996 | WIPO . |
| 96641873 | 12/1996 | WIPO . |

OTHER PUBLICATIONS

Cherng et al., Chemical Abstracts, vol. 125, No. 10, 1996, Abstract No. 123,570t.
Gorman et al., 1998, J. Biomed. Mater. Res. 39:642–649.
Kiser et al., 1998, Nature 394:459–462.
Meyer et al., 1998, FEBS Letts. 421:61–64.
Siegel, 1998, Nature 394:427–428.
Truong–Le et al., 1998, Human Gene Therapy 9:1709–1717.
Philippova et al., 1997, Macromolecules 30:8278–8285.
Kiser et al., 1997, Pro. AM. Chem. Soc. Div. Polymer Materials Sci. Eng., 76:226.
Schmid, 1997, Annu. Rev. Biochem. 66:511–548.
Tsujii et al. 1997, Macromolecules 30:7397–7402.
Mellman, 1996, Annu. Rev. Cell. Dev. Biol. 12:575–625.
Narayani and Rao, 1996, Int. J. Pharmaceutics 138:121–124.
M. Kashiwabara et al., 1995, Colloid Polym Sci 273:339–345.
Wadhwa et al., 1995, Bioconjugate Chemistry 6:283–291.
Jennifer L. Hill–West et al., 1994, American Fertility Society 62:630–634.
J C. Perales et al., 1994, Eur. J. Biochem.226:225–266.
Robinson, 1994, Curr. Opin. Cell Biol. 6:538–544.
Carelli Vera et al., 1993, International Journal of Pharmaceutics 94:103–113.
Carter et al., 1993, Jounral of Cell Biology 120:37–45.
Chang et al., 1993, EMBO Journal 12:2169–2180.
Gehrke, 1993, Adv. Polym.Sci. 110:81–144.
John Peeler et al., 1993, Journal of Cell Biology 120:47–54.
Ilavský, 1993, Adv. Polym. Sci. 109:173–206.
Kokufuta, 1993, Adv. Polym. Sci. 110:156–177.
Saito et al., 1993, Adv. Polym. Sci 109:207–232.
Schmid, 1993, Trends Cell Biol. 120:37–45.
Shibayama and Tanaka, 1993, Advances in Polymer Science 109:2–61.
Siegel, 1993, Advances in Polymer Science 109:233–267.
Suzuki, 1993, Adv. Polym. Sci. 110:199–240.
Verdugo, 1993, Adv. Polym. Sci. 110:145–156.
Brøndsted and Kopeček, 1992, in "Polyelectrolyte Gels", American Chemical Society, Washington, D.C., pp. 285–304.
Forgac, 1992, J. exp. Biol. 172:155–169.
Hunkeler and Hamielec, 1992, in "Polyelectrolyte Gels", American Chemical Society, Washington, D.C., pp. 24–41.
Mellman, 1992, J. Exp. Biol. 172:39–45.
Murphy et al., 1992, Biomaterials 13:979–990.
Smythe et al., 1992, J. Cell Biol. 119:1163–1171.
Tanaka, 1992, in "Polyelectrolyte Gels", American Chemical Society, Washington, D.C., pp. 1–21.
Siegel et al., 1991, Polym. Prep. 31:231–232.
You and Tirrell, 1991, American Cemical Society 113:4022–4023.

(List continued on next page.)

Primary Examiner—James Ketter
Attorney, Agent, or Firm—Lisa B. Kole

[57] ABSTRACT

The present invention relates to methods and compositions for delivery of a compound, most preferably a polynucleotide, into the cytoplasm of a cell by means of a microparticle, fabricated from a pH-sensitive hydrogel in collapsed phase, and having a size and physical characteristics compatible with uptake via a clathrin-coated pit on the cell surface. The trigger pH at which the hydrogel expands is lower than the physiological pH of the extracellular environment, allowing the microparticle, which comprises the compound to be delivered, to maintain its compact size prior to cellular uptake, thereby providing the additional benefit of protecting the comprised compound from degradation. This protective feature is particularly beneficial in embodiments in which a polynucleotide or a peptide is being delivered. Following uptake via a clathrin-coated pit, the microparticle then enters the intracellular endocytic pathway, where it is subjected to a progressive decrease in pH. Once the trigger pH for the hydrogel is reached, the microparticle increases its water content and expands, bursting its containing vesicle, and allowing its comprised compound to enter the cytoplasm. According to the invention, microparticle expansion and drug release may be achieved by natural mechanisms without requiring the addition of exogenous compounds, or the application of electric fields, etc. Moreover, with regard to embodiments involving polynucleotides, the present invention provides a means for traversing the plasma membrane and delivering the polynucleotide into the cytoplasm; in conventional transfection methods the plasma membrane, as well as intracellular membranes as occur in endosomes or lysosomes, constitute a formidable barrier to entry.

45 Claims, No Drawings

OTHER PUBLICATIONS

Brannon Peppas and Peppas, 1991, Chemical Engineering Science 46:715–722.
Huckett et al., 1990, Biochemcial Pharmacology 40:253–263.
Griffiths et al., 1989, Journal of Cell Biology 109:2703–2720.
Kornfeld and Mellman, 1989, Annu. Rev. Cell. Biol. 5:483–525.
Kou et al., 1988, Pharm. Res. 5:592–597.
Siegel and Firestone, 1988, Macromolecules 21:3254–3259.
Wu and Wu, 1988, Journal of Biological Chemistry 263:14621–14624.
Amiya and Tanaka, 1987, Macromolecules 20:1162–1164.
Ledley et al., 1987, J. Pediatrics 110:1–8.
Ukkonen et al., 1986, J. Exp. Med. 163:952–971.
Weiss et al., 1986, AICHE Symposium Series, "Recent Advances in Separation Techniques—III," 250 82:85–98.
Kielian and Helenius, 1985, Journal of Cell Biology 101:2284–2291.
Dipaola and Maxfield, 1984, J. Biol. Chem.259:9163–9171.
Chien et al., 1984, Polymer Journal 8:288–293.
Mellman and Plutner, 1984, Journal Cell Biol. 98:1170–1176.
Mellman and Ukonen, 1984, J. Cell Biol. 98:1163–1169.
Ricka and Tanaka, 1984, Macromolecules 17:2916–2921.
Maxfield and Yamashiro, 1987, Adv. Exp. Med. Biol.225:189–198.
Helenius et al., 1983, Trends Biochem, Sci. 8:245–250.
Marsh et al., 1983, Cell 32:931–940.
Nicolau et al., 1983, Proc. Natl. Acad. Sci. USA 80:1068–1072.
Steinman et al., 1983, Journal of Cell Biology 96:1–27.
White et al., 1983, Journal of Cell Biology 87:264–272.
Ungewickell and Branton, 1981, Nature 289:420–422.
Aisen and Listowsky, 1980, Annu, Rev. Biochem 49:367–393.
Kudela et al., 1980, J. Membrane Sci. 6:123–131.
Dabrozska et al., 1978, J. Biomed Mater. Res. 12:591–597.
Woodward and Roth, 1978, Proc. Natl Acad Sci, USA 75:4394–4398.
Krohn and Breitfeller, 1976, Invest. Ophthalmol. 15:324–327.
Crowther et al., 1976, J. Mol. Biol. 103:785–798.
Princiotto and Zapolski, 1975, Nature 255:87–88.
Vacik and Kopecek, J Appl. Polym. Sci. 19:3029–3044.
Kopeck et al., 1971, J. Polym Sci. 9:2801–2814.
Michaels, et al., 1961, J. Phys. Chem. 65:1765–1773.

EXPANDIBLE MICROPARTICLE INTRACELLULAR DELIVERY SYSTEM

1. INTRODUCTION

The present invention relates to methods and compositions for delivering a compound into the cytoplasm of a cell by means of an expandible microparticle comprising a matrix capable of rapid expansion and the compound to be delivered. The system of the invention may be used to deliver polynucleotides or peptides as well as conventional pharmaceutical compounds. As used in gene therapy applications, the expandible microparticles of the invention avoid many of the disadvantages associated with viral vectors and conventional transfection methods.

2. BACKGROUND OF THE INVENTION

2.1 CURRENT METHODS FOR INTRODUCING POLYNUCLEOTIDES INTO CELLS

Contemporary science has set, amongst its goals, the sequencing of the entire human genome, with the intention of using the genetic information obtained to further our understanding of physiology and to expand the opportunities for treatment of disease. One avenue of treatment currently being explored is the technique of gene therapy, in which a polynucleotide is introduced into a cell to confer a therapeutic benefit, for example, to provide a functional copy of a gene where the intrinsic gene is defective.

A number of methods have been conventionally used to introduce polynucleotides into cells, including calcium phosphate-DNA precipitation, electroporation, DEAE-dextran transfection, microinjection, and the use of a "gene gun" (see Australian Patent No. 9068389). Inefficiency of incorporation of polynucleotide and/or technical obstacles render each of these techniques problematic.

In hopes of improving polynucleotide delivery, viral vectors, including retrovirus, adenovirus, and adeno-associated virus vectors have been developed. Each of these three types of viral vectors, however, has serious disadvantages. Retroviruses insert polynucleotides only into cells which are actively dividing, and may act as insertional mutagens; adenovirus vectors provoke an immune response which eliminates vector from the host, thereby rendering any therapeutic benefit transient; and adeno-associated virus vectors are difficult to produce in large quantities (Marshall, 1995, Science 269:1050–1055; Paillard, 1998, Human Gene Therapy 9:1699–1700).

In order to avoid the disadvantages associated with viral vectors and conventional transfection methods, a number of alternative means and compositions for introducing nucleic acid into a cell have been devised. Such alternatives include lyophilized formulations of polynucleotide-lipid complexes (see, for example, International Patent Application Nos. PCT96US7867 and PCT 96US7866); polynucleotides linked to a dendrimer polycation (to improve transfection efficiency; U.S. Pat. No. 5,661,025); polynuclcotide compositions comprising a membrane-permeabilizing agent to transport the polynucleotide across the target cell membrane (International Patent Application No. PCT 93US3406); the use of polylysine as a DNA condensing agent (Wadhwa et al., 1995, Bioconjugate Chemistry 6:283–291), optionally linked to a carrier protein such as transferrin; and DNA trapped in liposomes (Ledley et al., 1987, J. Pediatrics 110:1) or in proteoliposomes (Nicolau et al., 1983, Proc. Natl. Acad. Sci. U.S.A. 80:1068). Receptor-mediated gene transfer techniques have been developed which rely on specific receptor/ligand interactions (Wu et al., 1988, J. Biol. Chem. 263:14621–14624; Christiano et al., 1993, Proc. Natl. Acad. Sci. U.S.A. 90:2122–2126; Huckett et al., 1990, Biochem. Pharmacol. 40:253–263; Perales et al., 1994, Eur. J. Biochem. 226:255–266). U.S. Pat. No. 5,589,466 by Felgner provides for the introduction of DNA into interstitial spaces, where it becomes available for cellular uptake. Truong-Le et al., 1998, Human Gene Therapy 9:1709–1717 report controlled gene delivery by DNA-gelatin microspheres having a size range of 200–700 nm, wherein transfection of cells was enhanced by incorporating chloroquine, which interferes with endosome acidification, into the microspheres.

It remains to be seen whether such methods and compositions will be successful in avoiding polynucleotide degradation, gaining access to the cytosol, and achieving sufficient proximity to the cell nucleus to result in efficient nuclear uptake.

2.2. CLATHRIN-COATED VESICLE MEDIATED UPTAKE AND TRANSPORT

In nature, there are two main mechanisms for internalization of substances: phagocytosis (literally, "cell eating"), in which relatively large particles (>0.5 $\mu$m diameter) are ingested, and pinocytosis ("cell drinking"), whereby smaller particles are internalized into small (<0.2 $\mu$m diameter) vesicles (reviewed in Mellman, 1996, Annu. Rev. Cell Dev. Biol. 12:575–625). Uptake by pinocytosis typically occurs at a specialized site in the plasma membrane referred to as a clathrin-coated pit (Id.).

Uptake of extracellular fluid and receptor-bound ligands is now known to occur via clathrin-coated pits, which serve as portals of entry into an intracellular system of vesicular organelles referred to as the "endocytic pathway". The endocytic pathway serves not only as a mechanism by which compounds in the extracellular space may enter cells, but also as a means for receptor recycling, as once a receptor releases its ligand in an internal vesicle, it may be returned to the cell surface via the pathway. Individual receptors have been estimated to be recycled at a rate of ten times per hour (Steinman et al., 1983, J. Cell. Biol. 96:1–27). This indicates that clathrin-mediated uptake and the endocytic pathway play a substantial and dynamic role in cell metabolism. Indeed, it has been reported that cells such as macrophages and fibroblasts internalize more than 200 percent of their entire surface area every hour (Id.).

A clathrin-coated pit closes around material to be internalized (referred to herein as its "cargo") by a series of molecular interactions and structural changes (discussed in greater detail in the next subsection), which result in a scaled, cargo-carrying clathrin-coated vesicle budding off the plasma membrane and entering the cytoplasm. Shortly after being internalized in this manner, the vesicle loses its clathrin coating and fuses with an early endosome (Helenius et al., 1983, Trends Biochem. Sci. 8:245–250). The primary role of early endosomes is to sort the "cargo" into molecules which are to be recycled (e.g. receptors which are to be sent back to the cell surface) or metabolized (in a lysosome; Mellman, 1996, Annu. Rev. Cell Dev. Biol. 12:575–625). Vesicles containing molecules which are to be metabolized are transferred to the perinuclear cytoplasm, where they fuse with late endosomes. The late endosomes, in turn, fuse with lysosomes, where the cargo is enzymatically digested.

The pathway from clathrin-coated vesicles to early endosomes, late endosomes and finally lysosomes is marked by a decrease in intra-vesicular pH (Mellman, 1992, J. Exp. Biol. 172:39–45). This decrease in pH is mediated by a V-ATPase, which promotes proton conduction across the vesicle membrane (Forgac, 1992, J. Exp. Biol. 172:155–169; Nelson, 1992, J. Exp. Biol. 172:149–153).

In early endosomes, the pH is mildly acidic (5.5–6.3), favoring release of receptor-bound ligand, but not sufficient to damage the receptor, thereby enabling recycling (Mellman, 1992, J. Exp. Biol. 172:39–45). It has been observed that many ligands dissociate from their receptors at pH less than 7 (Maxfield and Yamashiro, 1987, Adv. Exp. Med. Biol. 225:189–198). At pH less than 6, iron is released from differic transferrin (IdI., Princioto and Zapolski, 1975, Nature 255:87; Aisen and Listowsky, 1980, Annu. Rev. Biochem. 49:367), and the epidermal growth factor receptor undergoes a large scale conformational change which releases its ligand (Maxfield and Yamashiro, supra, DiPaola and Maxfield, 1984, J. Biol. Chem. 259:9163).

Progressing along the endocytic pathway, the intravesicular environment becomes more favorable to cargo degradation. The pH of late endosomes is generally less than 5.5, and the lysosomal pH may be as low as 4.6 (Mellmaii, 1992, J. Exp. Biol. 172:39–45; Komfeld and Mellman, 1989, Annu. Rev. Cell Biol. 5:483–525). Moreover, the content of acid hydrolases increases (Id.). Sometimes the cargo being degraded is a receptor; one mechanism of receptor down-regulation is the destruction of ligand-receptor complexes in lysosomes (as observed for the Fe receptor bound to IgG; Mcllman and Plutner, 1984, J.Cell. Biol. 98:1170–1176; Mellman and Ukkonen, 1984, J. Cell Biol. 98:1163–1169; Ukonnen et al., 1986, J. Exp. Med. 163:952–971).

In addition to its role in uptake of molecules and receptor recycling, the endocytic pathway is exploited by certain pathogenic agents, including diphtheria toxin and various viruses, such as influenza virus and Semliki Forest virus (Maxfield and Yamashiro, 1987, Adv. Exp. Med. Biol. 225:189–198; Olsnes and Sandvig, 1983, in "*Receptor-inediated Endocytosis: Receptors and Recognition*", Cuatrecasa and Roth, eds., Chapman & Hall, London, pp. 187–236; Klielian and Helcnius, 1985, J. Cell Biol. 101:2284; White et al., 1980, J. Cell Biol. 87:264; Marsh et al., 1983, Cell 32:931). At acidic pH, the toxin or viral coat protein, as the case may be, undergoes a conformational change which permits its passage out of the vesicle and into the cytosol.

Entry into and passage through the endocytic pathway is a rapid process which involves a significant portion of the intracellular volume. By following the progress of the fluid phase marker horseradish peroxidase ("HRP"), it was found that, for the first two minutes after exposure of a baby hamster kidney cell to HRP, the volume density of labeled structures increased rapidly, and then remained constant for the next 13–18 minites at a plateau level accounting for approximately 0.65 percent of the cytoplasmic volume (Griffiths et al., 1989, J. Cell Biol. 109 :2703–2720). Subsequently, the volume density again increased rapidly (as HRP reached the lysosomal compartment), to reach a second plateau between 30 and 60 minutes of labeling, to constitute 3.5 percent of the cytoplasmic volume (Id.).

2.3. MOLECULAR ASPECTS OF CLATHRIN-COATED VESICLE FORMATION

A number of molecules participate in the formation of clathrin-coated vesicles from the plasma membrane, including, in addition to clathrin, AP2 (for "adaptor protein" or "assembly protein") and dynamin (reviewed in Schmid, 1997, Annu. Rev. Biochem. 66:511–548). Upon binding, AP2 triggers assembly of a clathrin lattice (Id.). Dynamin, a GTPase, promulgates structural changes which result in the sealing and budding of the clathrin-coated vesicle from the plasma membrane (Id.).

Clathrin is a protein complex consisting of three 192 kDa heavy chains, each bound to either of two different light chains having molecular weights of approximately 30 kDa. The complex is referred to as a "triskelion" because it has a three-legged appearance (Kirchhausen et al., 1986, J. Ultrastructur. Mol. Struct. Res. 94:199–208; Ungewickelland and Branton, 1981, Nature 289:420–422). In solution, clathrin triskelions self-assemble to form closed polyhedral structures called "cages" (Crowther et al., 1976, J. Mol. Biol. 103:785–798; Woodward, 1978, Proc. Natl. Acad. Sci. U.S.A. 75:4394–4398). In the plasma membrane, polyhedral assemblies of clathrin form coated pits which increase in curvature as cargo from the extracellular environment is engulfed; it is believed that the shape changes in the clathrin pit required for invagination involve the incorporation of pentagonal arrangements of triskelions in an otherwise hexagonal array (Schmid, 1997, Annu, Rev. Biochem. 66:511–548).

AP2 plays a critical role in the attachment of clathrin to membranes, being first recruited to the membrane surface in order to provide a binding site for clathrin (Mellman, 1996, Annu. Rev. Cell Dev. Biol. 12:575–625; Chang et al., 1993, EMBO J. 12:2169–2180; Peeler et al., 1993, J. Cell. Biol. 120:47–54; Robinson, 1994, Curr. Opin. Cell Biol. 6:538–544; Traub et al., 1995, J. Biol. Chem. 270:4933–4942). Moreover, AP2 recruits membrane proteins for uptake by means of a diversity of molecular localization signals comprised in molecules (such as receptors) destined to be clathrin-coated vesicle cargo; a number of such signals have been characterized (Mellman, 1996, Annu. Rev. Cell Dev. Biol. 12:575–625). Broadly defined peptide consensus sequences may include aromatic (usually tyrosine) residues in proximity to one or more amino acids with large hydrophobic side chains (Trowbridge et al., 1993, Annu. Rev. Cell Biol. 9:129–161), or vicinal leucine residues (or leucine and another small hydrophobic amino acid), the latter being favored among receptors expressed in leukocytes (Matter et al., 1994, J. Cell. Biol. 126:991–1004; Hunziker and Fumey, 1994, EMBO J. 13:2963–2967).

Although its role is not yet completely understood, dynamin, in its GDP-bound state, is believed to interact with the clathrin lattice of an invaginated coated pit, whereupon binding of GTP triggers redistribution of the dynamin to form a constricted neck at the plasma membrane, thereby initiating the budding process. GTP hydrolysis then drives a tightening of the neck, resulting in the detachment of a sealed clathrin-coated vesicle into the cytoplasm. The diameter of the clathrin-coated vesicle is approximately 80–100 nm (.08–0.1 $\mu$m; Griffiths et al., 1989, J. Cell Biol. 109:2703–2720).

2.4. pH SENSITIVE HYDROGELS

A hydrogel is a three-dimensional polymeric network (i.e., matrix) containing a substantial (usually greater than 20 percent) amount of water (Brøndsted and Kopeček, 1992, in "Polyelectrolyte Gels", American Chemical Society, Washington, D.C., pp. 285–304; Wichterle and Lim, 1960, Nature 185:117). Because of their high water content, hydrogels tend to be compatible with biological systems and therefore have been used in various medical applications, including tissue implants, soft contact lenses, and drug delivery systems (Mack et al., 1987, in "*Hydrogels in Medicine and Pharmacy*", Peppas, ed., CRC Press, Boca Raton, Fla., vol. III, pp. 65–93).

Polymeric hydrogels can exist in two distinct phases: collapsed (also referred to as contracted, condensed, or compressed) and expanded (also referred to as swollen or decompressed). Volume transition occurs between these phases either continuously (gradually) or discontinuously (abruptly), depending on the nature of the polymer and a variety of other factors, including temperature, solvent composition, pH, ionic composition, electric field, and light. When a hydrogel expands, it absorbs water.

Phase transitions in gels have been of particular interest recently, and gels have been developed which expand or contract as necessary to serve a variety of purposes, including providing a superabsorbent diaper, facilitating drug delivery, and mimicking muscle contraction (see, for example, Tanaka, 1992, in "Polyelectrolyte Gels", American Chemical Society, Washington, D.C., pp. 1–21). Discontinuous phase transition may potentially result in a thousand-fold or greater change in gel volume.

Discontinuous phase transition results from an imbalance between attractive (collapsing) and repulsive (expanding) interactions between the polymer constituents of a gel. Such interactions may be ionic, hydrophilic/hydrophobic, van der Waals, or hydrogen-bonding in character (Id.). Electrostatic (ionic) interactions between moieties in the polymer may act as particularly powerful forces to expand or collapse a gel. For example, if a gel having uncharged moieties (e.g., $—NH_2$) is placed in conditions (e.g., acidic pH) which render its moieties similarly charged (e.g., $—NH_3^+$), the consequent electrostatic repulsive interaction will act like an internal pressure, and the gel will expand rapidly in order to increase the distance between the like charges. Hydrogols that undergo phase transition in response to changes in pH typically contain pendant acidic or basic groups, such as carboxylic acids and primary amines, or strong acids and bases, such as sulfonic acids and quateniary ammonium salts, which change ionization state as pH increases or decreases (Brøndsted and Kopeček, 1992, in "Polyelectrolyte Gels", American Chemical Society, Washington, D.C., pp. 285–304; Kopeček et al., 1971, J. Polym. Sci. 9:2801).

When used in the context of drug delivery, hydrogels are believed to permit the diffusion of drugs in and out of the gel by, in the case of hydrophilic low molecular weight drugs, a "pore mechanism", and, for more hydrophobic compounds, a "partition mechanism", The permeability of various compounds, up to a molecular weight of 70,000 Da, through lyophilized polyacrylonitrile was observed (Dabrovska et al., 1978, J. Biomed. Mater. Res. 12:591). The extent of cross-linking has been found to be important for pH-dependent permeability (Weiss et al., 1986, AIChE Symposium Series 82:85). It has also been observed that by adding hydrophobic groups to a pH-sensitive hydrogel, the pH change required for phase transition may be increased (by stabilization of the collapsed phase; Philippova et al., 1997, Macromolecules 30:8278–8285).

Recently, Kiser et al. (1998, Nature 394:459–462) produced a synthetic mimic of a naturally occun-ing secretory granule in the form of a microsphere fabricated from a pH and ion-sensitive polymer containing the anti-cancer drug doxorubicin hydrochloride, protecting the microspheres from pH changes with a lipid bilayer coating (U.S. Pat. No. 5,654,006 by Fernandez and Knudson). The lipid bilayer could be breached to result in drug release by placing the particle in an electroporation field (see also Siegel, 1998, Nature 394:427–428).

3. SUMMARY OF THE INVENTION

The present invention relates to methods and compositions for delivery of a compound, most preferably a polynucleotide, into the cytoplasm of a cell by means of a microparticle, fabricated from a pH-sensitive hydrogel in collapsed phase, and having a size and physical characteristics compatible with uptake via a clathrin-coated pit on the cell surface. The trigger pH at which the hydrogel expands is lower than the physiological pH of the extracellular environment, allowing the microparticle, which comprises the compound to be delivered, to maintain its compact size prior to cellular uptake, thereby providing the additional benefit of protecting the comprised compound from degradation. This protective feature is particularly beneficial in embodiments in which a polynucleotide or a peptide is being delivered.

Following uptake via a clathrin-coated pit, the microparticle then enters the intracellular endocytic pathway, where it is subjected to a progressive decrease in pH. Once the trigger pH for the hydrogel is reached, the microparticle increases its water content and expands, bursting its containing vesicle, and allowing its comprised compound to enter the cytoplasm.

According to the invention, microparticle expansion and drug release may be achieved by natural mechanisms without requiring the addition of exogenous compounds, or the application of electric fields, etc. Moreover, with regard to embodiments involving polynucleotides, the present invention provides a means for traversing the plasma membrane and delivering the polynucleotide into the cytoplasm; in conventional transfection methods the plasma membrane, as well as intracellular membranes as occur in endosomes or lysosomes, constitute a formidable barrier to entry.

4. DETAILED DESCRIPTION OF THE INVENTION

The present invention provides for a microparticle comprising a pH-sensitive hydrogel in a collapsed state and containing a compound to be delivered to the interior of a cell, wherein the microparticle is of a size, in the collapsed state, which allows uptake of the microparticle via a clathrin-coated pit on the cell surface, and wherein the hydrogel expands at a pH less than 7.

The present invention provides for a method for delivering a compound to the interior of a cell, comprising introducing a microparticle containing the compound into the endocytic pathway of the cell, wherein the microparticle comprises a pH-sensitive hydrogel in a collapsed state prior to its introduction into the endocytic pathway, but which assumes an expanded state within the endocytic pathway, thereby delivering the compound into the interior of the cell.

The term "collapsed state", as used herein, refers to the condition of the pH-sensitive gel when it encounters the clathrin-coated pit of its intended target cell. The "expanded state" of the pH-sensitive gel is the condition of the pH-sensitive gel when it has entered the endocytic pathway and reached its maximal expansion in that environment. These definitions are made to clearly describe the size of the microparticles as they are used according to the invention, with the understanding that such microparticles, under other conditions, may collapse or expand further. Where a microparticle is collapsed to a greater extent than that defined as the "collapsed state" (for example, in an alkaline pH, lyophilized, or in a particular solvent), it is said to be in a "super-collapsed state". Conversely, where a microparticle is expanded to a greater extent than that defined as the "expanded state" (for example, in a highly acid system, at high temperatures, or in a particular solvent), it is said to be in a "super-expanded state".

The size of the microparticle, in its collapsed state, is of a dimension which allows its uptake, via a clathrin-coated pit, into the endocytic pathway. To give particular nonlimiting examples, a microparticle of the invention may have a diameter of 50–150 nm (0.05–0.15 µm), preferably 50–100 nm (0.05–0.1 µm), and more preferably 50–70 nm (0.05–0.07 µm) (all intervals herein being inclusive of their limits unless expressly noted otherwise). Because, in a batch of microparticles, there are likely to be microparticles which vary somewhat in size, the use of a composition comprising microparticles having a range of sizes, including some which may exceed the diameter of the clathrin-coated pit, is contemplated.

The microparticle, in the expanded state which it achieves following cellular uptake, should have a size large enough to burst its containing vesicle, but not so large as to destroy the structural or functional integrity of the cell. In this regard, it should be noted that early endosomes have approximate diameters of 100–400 nm (0.1–0.4 µm) and large late endosomes and lysosomes may have a diameter of up to about 3000 nm (3 µm), the diameter of a cell being on the order of approximately 10,000 nm–50,000 nm (10–50 µm), with a great deal of variability among different types of cells. The invention is not limited to a particular physical mechanism by which the vesicle is burst, provided that it is related to expansion of the microparticle; for example, expansion may result in bursting where the volume of the expanded microparticle exceeds the volume of the vesicle, or expansion of the microparticle may create a structural defect in the vesicle membrane which results in its rupture. As a non-limiting example, a microparticle adherent to the inner surface of the membrane of its containing vesicle may tear this membrane as it expands.

Accordingly, in non-limiting examples of the invention, the diameter of the microparticle, in its expanded state, may preferably be 5–10 fold greater than its diameter in the collapsed state, where expansion occurs in early endosomes, and, where expansion occurs in late endosomes or lysosomes, the diameter of the microparticle in the expanded state may preferably be increased by a factor of 10–100. The present invention further contemplates expansion by a factor of greater than 100, where such expansion does not destroy the cell into which the compound is intended to be delivered.

For purposes of clarity of disclosure, and not by way of limitation, the remainder of this detailed description is divided into the following subsections:

(i) pH-sensitive hydrogels;

(ii) microparticle preparation; and (iii) uses of expandible microparticles.

4.1. pH-SENSITIVE HYDROGELS

The microparticles of the invention are comprised of an expandible matrix and a compound to be delivered to the interior of a cell (i.e., within the boundary created by the outer plasma membrane of the cell), where the compound is either dispersed continuously or discontinuously within the matrix.

Hydrogels which may be used as the matrix for microparticles are in an expanded state at pH less than 7. The pH at which expansion within the endocytic pathway sufficient to rupture the containing vesicle occurs is referred to as the "trigger pH". Preferably, the phase transition of the hydrogel as it expands in the cell is discontinuous, in which case the pH at which the transition occurs is referred to as the "critical pH" (so that the "critical pH" is a particular species of "trigger pH"). Depending on the intended use of the microparticle of the invention, a hydrogel may be selected such that the trigger pH conforms with the pH of a vesicle in the intracellular location where expansion of the hydrogel is desired. In non-limiting examples, if expansion in early endosomes is desired, a hydrogel having a trigger pH within the range of 5.5–6.3 may be used; if expansion in late endosomes is desired, a hydrogel having a trigger pH within the range of 5.0–5.5 may be selected; and if expansion in lysosomes is desired, the trigger pH may be less than or equal to 5.0. Where delivery of a polynucleotide is desired, it may be advantageous to produce expansion relatively late in the endocytic pathway, as late endosomes and lysosomes are in closer proximity to the cell nucleus. pH-sensitive hydrogels which may be used according to the invention are those which contain one or more ionic or ionizable moiety in the polymeric backbone and/or in crosslinks (see, for review, Brøndsted and Kopeček, 1992, in "Polyelectrolyte Gels", American Chemical Society, Washington, D.C., pp. 285–304), wherein the predominant ionic or ionizable moiety is basic, that is, positively charged at acidic pH, in order to drive expansion of the matrix by electrostatic repulsion between positively charged ions. Non-limiting examples of such basic moieties are amines, including the moieties —$NH_2$, —$N(CH_3)_2$, —$N(CH_2CH_3)_2$, vinylpyridine, moieties comprising imidazole or an imidazole derivative and —$N(CH_3)_3^+$, to name but a few. However, acidic moieties may, in certain embodiments, also be present, but preferably should not constitute the predominant charged moieties at a given acidic pH. Hydrogels in which acidic and basic moieties are both present are referred to as polyelectrolyte hydrogels. In one specific non-limiting embodiment of the invention, where the compound to be delivered is a polynucleotide (which tends to be negatively charged), a polyelectrolyte hydrogel may be advantageously used as the microparticle matrix, because, after expansion of the microparticle has occurred and the expanded microparticle is in the relatively pH neutral cytosol, the presence of negatively-charged acidic moieties may facilitate the release of polynucleotide from the particle. Similar considerations may be applied regarding the compatibility of a hydrogel with any other compound(s) to be delivered, in terms of not only electrostatic interactions but also van der Waals forces, hydrophilic/hydrophobic interactions and hydrogen bonding, in order to provide for effective retention and release of the compound(s).

A pH-sensitive hydrogel used as a matrix in a microparticle of the invention, in addition to having an appropriate trigger pH and a physicochemical profile compatible with the drug to be delivered, should swell to an expanded state which has dimensions consistent with the size restrictions set forth above. Further, once the microparticle is in its expanded state in the cell, having burst its containing vesicle, the microparticle preferably collapses at a rate slower than its expansion (a phenomenon referred to as "hysteresis") in order to facilitate release of the contained compound. With regard to polyelectrolyte gels which swell in mildly acidic pH, it is reported that it has not been possible to fully deswell such gels back to their nearly dry state by simply varying the pH (Seigel, 1993, Adv. Polymer Sci. 109:233–267), indicating that deswelling of the expanded microparticle in the cytoplasm would not be expected to substantially interfere with compound delivery.

Factors which influence the swelling of a pH-sensitive hydrogel comprising ionic or ionizable moieties include (i) the charge of the moiety (Kopeček et al., 1971, J. Polym. Sci.9:2801; Vacik et al., 1975, J. Appl. Polym. Sci. 19:3029); the pKa of the moiety (Brannon-Peppas and Peppas, 1991, Chem. Eng. Sci. 46:715); the degree of ionization; the concentration of ionizable moiety; the cross-linking density (Kou et al., 1988, Pharm. Res. 5:592); and the hydrophilicity/hydrophobicity of the polymer backbone. Factors within the endocytic pathway which may influence swelling include the pH (Siegel and Firestone, 1988, Macromolecules 21:3254); the ionic strength, and the presence and valency of counterions (Siegel et al., 1991, Polym. Prep. 31:231; Siegel, 1990, in "Pulsed and Self-regulaled Drug Delivery", Kost, ed., CRC Press, Boca Raton, Fla. pp. 129–157).Discontinuous phase transitions in hydrogels of the invention may be induced by varying the ionic composition (Ohmine and Tanaka, 1982, J. Chem. Phys. 77:5725; Shibayama and Tanaka, 1993, Adv. Polym. Sci. 109:1–61).

If it is found that, all other parameters being compatible with an intended microparticle formulation, the trigger pH of a hydrogel is at a higher pH than would be desired, hydrophobic repeat units may be incorporated into the hydrogel to result in expansion at a lower pH (Philippova et al., 1997, Macromolecules 30:8278–8285).

In non-limiting specific embodiments of the invention, a pH-sensitive hydrogel used in the preparation of a microparticle may comprise the following basic monomer units (in the context of the polymer): aminoethyl methacrylate; N,N-dimethylaminoethyl methacrylate (Siegel and Firestone, 1988, Macromolecules 21:3254; Siegel, 1990, in "Pulsed and Self-regulated Drug Delivery", Kost, ed., CRC Press, Boca Raton, Fla., pp. 129–157); N,N-diethylaminoethyl methacrylate (Kopeček et al., 1971, J. Polym. Sci.9:2801; Vacik and Kopeček, 1975, J. Appl. Polym. Sci. 19:3029; Ishihara et al., 1984, Polymer J. 8:625); a moiety comprising imidazole; a moiety comprising an imidazole derivative; vinylpyridine; and vinylbenzyl trimethylammonium chloride (Michaels et al., 1961, J. Phys. Chem. 65:1765; Michaels, 1965, Ind. Eng. Chem. 57:32).

In further non-limiting specific embodiments of the invention, a pH-sensitive hydrogel used in the preparation of a microparticle may comprise the following acidic monomer units (in the context of the polymer): acrylic acid or methacrylic acid (Ricka and Tanaka, 1984, Macromolecules 17:2916; Kopeček et al., 1971, J. Polym. Sci.9:2801; Kou et al., 1988, Pharm. Res. 5:592; Vacik and Kopeček, 1975, J. Appl. Polym. Sci. 19:3029); alkyl methacrylate esters, and particularly methylmethacrylate ester (Siegel and Firestone, 1988, Macromolecules 21:3254–3259); sodium styrencsulfonate (Michaels et al., 1961, J. Phys. Chem. 65:1765; Michaels, 1965, Ind. Eng. Chem. 57:32); and sulfoxyethyl methacrylate (Kudela et al., 1980, J. Membrane Sci. 6:123).

In still further non-limiting specific embodiments of the invention, a pH-sensitive hydrogel used in the preparation of a microparticle may comprise a polyelectrolyte complex formed from an anionic polymer and a cationic polymer, where, at pH less than 7, cations are the predominant ionic species, and the polymer pairs may be as follows: poly (vinylbenzyl trimethylammonium chloride) and sodium poly(styrene sulfonate) (Ratner and Hoffman, 1976, in "Hydrogels for Medical anid Related Applications", Andrade, ed., ACS Symposium Series 31, American Chemical Society, Washington, D.C., pp. 1–36); and copolymers based on n-alkyl methacrylate esters and (dimethylamino) ethyl methacrylate (Siegel and Firestone, 1988, Macromolecules 21:3254–3259).

In yet further embodiments of the invention, the hydrogel may become soluble in the expanded state. Acrylic water-soluble polymers are described in Hunkeler and Hamielec, 1992, "Polyelectrolyte Gels", Americal Chemical Society, Washington, D.C., pp. 24–41; other references relating to soluble hydrogels include Hill-West et al., 1994, Fertility and Sterility 62:630–634 and Murphy et al., 1992, Biomaterials 13:979–990. A water-soluble gel may lack covalent cross-links. References relating to non-cross-linked hydrogcls include Gornan et al., 1998, J. Biomed. Mat. Res. 39:642–649; Narayani and Rao, 1996, Int. J. Pharmaceutics 138:121–124; Carelli et al., 1993, Int. J. Pharmaceutics 94:103–113; and Krohn and Breitfeller, 1976, Invest. Ophthalmol. 15:324–327. Solubility may in some cases desirably facilitate the release of compound to be delivered.

In one preferred, non-limiting specific embodiment of the invention, the pH-sensitive hydrogel used in the preparation of a microparticle is a lightly-cross-linked polyclectrolyte copolymer based on n-methylmethacrylate ester and (dimethylamino)ethyl methacrylatc, at a comonomer ratio of 70:30, as described in Siegel and Firestone, 1988, Macromolecules 21:3254–3259 and Siegel, 1993, Adv. Polymer Sci. 109:233–267).

4.2. MICROPARTICLE PREPARATION

Microparticles of the invention may be prepared by first forming pH-sensitive hydrogel microparticles, and then incorporating the compound to be delivered, or, alternatively, by incorporating the compound simultaneously with microparticle formation by including the compound in the system in which the hydrogel is polymerized.

pH-sensitive hydrogcl microparticles may be formed by any method known in the art, provided that the resulting microparticles, in the collapsed state, have appropriate dimensions for clathrin-coated pit uptake, as set forth above.

In one non-limiting example of a technique of microparticle preparation, referred to as "precipitation polymerization", the constituent monomers are dissolved in a solvent in which the product polymer is insoluble, and then the dissolved monomers are subjected to a polymerization initiator (which may be a chemical compound or a physical agent such as light), under conditions of vigorous mixing. The combination of insolubility of the polymer and the agitation of the solution result in microparticle formation. Using this technque, the size of microparticles produced may be controlled by the length of time that the reaction is allowed to proceed and by the amount of cross-linking (Kashiwabara et al., 1995, Colloid Polymer Science 273:339–345; U.S. Pat. No. 5,654,006 by Fernandez; Kawaguchi et al., 1991, Polymer J. 23:955–962; Kawaguchi et al., 1993, Polym. Inteml. 30:225–236).

Another method by which microparticles may be prepared in the technique referred to as "emulsion polymerization", in which monomers are dissolved in a continuous aqueous phase also containing emulsifier micelles plus excess free monomer stored in large droplets in suspension. When the system is subjected to an initiator, polymerization occurs in the regions of the micelles (Kreuter, 1992, in "Microcapsules and Nanoparticles in Medicine and Phariacy", CRC Press, Boca Raton, Fla.; Hunkaler and Hamielec, 1992, in "Polyelectrolyte Gels", American Chemical Society, Washington, D.C., pp. 24–41). In a related technique referred to as "emulsion polymerization in continuous organic phase", water soluble monomers are added to a water-in-oil emulsion stabilized by a surfactant, under conditions such that polymerization is initiated in the aqueous phase droplets (Kreuter, 1992, in "Microcaipsules and Nanoparticles in Medicine and Pharmacy", CRC Press, Boca Raton, Fla.).

Where the compound to be delivered is incorporated subsequent to microparticle formation, the hydrogel microparticle may be exposed to a solution containing the compound, thereby permitting diffusion of the compound into the gel matrix. High concentrations of the compound, and a pH of the solution in which the microparticle is swollen, may favor incorporation. As a specific non-limiting example, the hydrogel microparticle may be placed in an aqueous solution of polynucleotide having a pH of 5–6 and containing the compound to be incorporated. After the microparticle is loaded with the desired amount of compound, the pH of the solution may be increased so that hydrogel condenses and the size of the microparticle decreases.

Compounds which may be incorporated into the microparticles of the invention include compounds which are desirably delivered into the cytoplasm and which have a molecular size and chemical character which permits their retention in and release from a hydrogel microparticle as described herein. For example, the invention may be used to deliver compounds which are extremely hydrophilic and therefore have limited membrane permeability. In non-limiting specific embodiments of the invention, the compound is a polynucleotide. Further, the microparticles of the invention may be used to deliver a factor (e.g., a peptide) which typically enters a cell via a specific receptor, thereby circumventing the limitations of receptor location and saturation. In yet additional embodiments of the invention, the compound to be delivered may be an immunogenic peptide, protein, or adjuvant.

One or more compound to be delivered may be incorporated into a microparticle of the invention.

A polynucleotide which may be delivered according to the invention may be a DNA or a RNA molecule, and may be single-stranded or double stranded. The polynucleotide preferably has a size of less than fifty kilobases (50 kb), in order to permit its effective release from the microparticle, but the invention is not so limited. Polynucleotide may be prepared by chemical synthesis or by recombinant techniques, or may be prepared from nucleic acid harvested from a natural source. The polynucleotide may encode a RNA or protein desirably produced in the cell, may have ribozyme activity, may act in an antisense capacity, and/or may bind to protein factors in the cell. The polynucleotide may therefore comprise one or more functional subregions, including a promoter element, ribosome binding site, polyadenylation site, etc. Where it is desired that the polynucleotide enter the cell nucleus, a nuclear targeting sequence may be included.

The microparticles of the invention, in addition to the hydrogel matrix and compound to be delivered, may comprise other elements, including, but not limited to, elements which improve the efficiency of uptake by clathrin-coated pits. As a non-limiting example, a targeting molecule, which may be incorporated into the microparticle or attached to its surface by covalent or noncovalent means, may be used in this capacity. A targeting molecule according to the invention is a molecule which binds to a cell-surface molecule that is internalized by endocytosis. Non-limiting examples of targeting molecules include carbohydrate moieties such as mannose, mannose-6-phosphate, mannose-6-phosphonate, and carbohydrate ligands for cellular lectins, as well as other binding partners for cellular receptors, such as insulin, epidermal growth factor, or immunoglobulin heavy chain; binding portions or analogs of the foregoing molecules may also be used for targeting purposes. The choice of targeting molecule may aid in the selective incorporation of microparticles into a particular subpopulation of cells. For example, in a specific non-limiting embodiment of the invention, where introduction of a microparticle into a dendritic cell is desired (e.g., where a microparticle is to deliver an immunogenic peptide, protein or adjuvant or a polynucleotide encoding an immunogenic peptide, protein, etc. to be used in antigen presentation), the microparticle may comprise a mannose moiety as a targeting molecule, since dendritic cells have surface mannose receptors.

Various assays may be used to determine whether a microparticle according to the invention is amenable to cellular uptake. Non-limiting examples of suitable assays include those described in Schmid, 1997, Annu. Rev. Biocehm. 66:511–548; Smythe et al., 1992, J. Cell Biol. 119:1163–1171; Smythe et al., 1989, J. Cell Biol. 108:843–853; Schmid and Smythe, 1991, J. Cell Biol. 114:869–880; Carter et al., 1993, J. Cell Biol. 120:37–45; and Schmid, 1993, Trends Cell Biol. 3:145–148, each of which are incorporated by reference in their entireties herein. For example, incorporation of microparticles may be assessed in semi-intact or perforated cells whose plasma membrane has been ruptured by mechanical shear, by evaluating the degree of inaccessibility of the microparticles (an indication of sequestration in the cytosol) to a probe directed at the microparticle. Alternatively, progress of microparticles into and through the endocytic pathway may be monitored by electron microscopy or (where the microparticle comprises a polynucleotide) in situ hybridization or hybridization to nucleic acid in cellular subfractions.

4.3. USES OF EXPANDIBLE MICROPARTICLES

The expandible microparticles of the invention may be used to be deliver compounds such as pharmaceuticals, peptides, and polynucleotides into the cytoplasm of a cell. These compounds may be delivered for therapeutic, diagnostic, research, or industrial purposes.

The present invention provides for compositions comprising the expandible microparticles described above. Such compositions may be in a variety of physical forms, including liquid, aerosol, emulsion and solid forms, and may comprise various other agents compatible with the intended use of the microparticles. As specific, nonlimiting examples, micorparticles of the invention may be stored in a dry, powder form which is reconstituted prior to use; or, microparticles may be comprised in a liquid composition which further comprises one or more buffering agents which maintain the microparticles in a condensed conformation (e.g., the microparticles may be stored in an alkaline pH buffer solution which induces a super-collapsed state).

The present invention further provides, in non-limiting embodiments, for compositions comprising mixtures of microparticles which may differ in their hydrogel matrix and/or compound(s) to be delivered. Such mixtures may be useful in delivering one or more compound to the interior of a cell, or in introducing one or more compound at different points of the endocytic pathway.

A cell may be contacted with expandible microparticles of the invention via a variety of modes of administration, which may be performed in vitro or in vivo. When administered to the cell in vivo, in the context of the organism in which the cell is comprised, the microparticles may be administered by intravenous, intraarterial, intrathecal, intraperitoneal, intramuscular, intradermal, subcutaneous, intranasal, rectal, pulmonary, or topical routes, etc. With regard to oral administration, the microparticles of the invention may require a coating which prevents expansion of the microparticles in the acidic pH of the gastrointestinal tract.

In certain non-limiting specific embodiments of the invention in which the compound to be delivered is a polynucleotide, it is contemplated that the methods of the invention may be used in the treatment of inherited diseases, whereby the undesirable effect of a defective endogenous nucleic acid is corrected or ameliorated, or the treatment or prevention acquired diseases, including infectious diseases, malignancies, autoimmune diseases, degenerative disorders, and disorders associated with aging.

As one specific, non-limiting example, a polynucleotide encoding an antigen associated with a pathogen or a malignancy may be introduced into a cell of a subject via a microparticle of the invention, thereby effecting genetic vaccination which protects against or treats infection with the pathogen or development or progression of the malignancy.

In a related embodiment of the invention, a microparticle may be used to introduce one or more immunogenic peptide, protein or adjuvant into a cell. In such embodiments, where the microparticle bursts its containing vesicle, the peptide, protein or adjuvant may be processed according to the class I pathway, and be presented on the cell surface in the context of major histocompatibility class I antigen. If, however, the microparticle expands sufficiently to deliver its contained immunogenic peptide, protein, or adjuvant but insufficiently to burst its containing vesicle (a specific non-limiting embodiment of the invention), the immunogenic peptide, protein, or adjuvant may be released into the vesicle and be processed according to the class II pathway, and be presented on the cell surface in the context of major histocompatibility class II antigen. In this manner, an immune response directed toward class I and/or class II antigens may be induced.

It is further envisioned that the microparticles of the invention may be used in the introduction of polynucleotides into non-human animals, including domesticated animals, such as livestock and pets, as well as non-domesticated animals, in which expandible microparticles comprising a polynucleotide may be introduced into one or more cells of either (i) a non-human animal embryo; or (ii) a juvenile or adult non-human animal. As specific, non-limiting examples, such microparticles may be used in the genetic engineering of non-human animal embryos, or in the genetic vaccination of domestic animals or wild animal populations.

Various publication are cited herein, the contents of which are hereby incorporated by reference in their entireties.

I claim:

1. A microparticle comprising a pH-sensitive hydrogel in a collapsed state and containing a compound to be delivered to the interior of a cell, wherein the microparticle is of a size, in the collapsed state, which allows uptake of the microparticle via a clathrin-coated pit on the cell surface, and wherein the pH-sensitive hydrogel expands at a pH less than 7 to result in a microparticle comprising the pH-sensitive hydrogel in an expanded state.

2. The microparticle of claim 1, wherein the microparticle comprising the pH-sensitive hydrogel in the expanded state has a diameter which is between five and ten times greater than the diameter of the microparticle comprising the pH-sensitive hydrogel in the collapsed state.

3. The microparticle of claim 1, wherein the microparticle comprising the pH-sensitive hydrogel in the expanded state has a diameter which is between ten and one hundred times greater than the diameter of the microparticle comprising the pH-sensitive hydrogel in the collapsed state.

4. The microparticle of claim 1, wherein the microparticle comprising the pH-sensitive hydrogel in the expanded state has a diameter which is more than one hundred times greater than the diameter of the microparticle comprising the pH-sensitive hydrogel in the collapsed state.

5. The microparticle of claim 1, wherein the ph-sensitive hydrogel expands at a pH of 5.5–6.3.

6. The microparticle of claim 1, wherein the pH-sensitive hydrogel expands at a pH of 5.0–5.5.

7. The microparticle of claim 1, wherein the pH-sensitive hydrogel expands at a pH of less than 5.0.

8. The microparticle of claim 1, having a diameter of 50–150 nm.

9. The microparticle of claim 1, wherein the pH-sensitive hydrogel comprises a basic monomer unit selected from the group consisting of aminoethyl methacrylate, N,N-dimethylaminoethyl methacrylate, N,N-diethylaminoethyl methacrylate, vinylpyridine, a moiety comprising imidazole, a moiety comprising an imidazole derivative and vinylbenzyl trimethylammonium chloride.

10. The microparticle of claim 1, wherein the pH-sensitive hydrogel comprises a basic monomer unit and an acidic monomer unit selected from the group consisting of acrylic acid, methacrylic acid, methyl methacrylate ester, sodium styrenesulfonate and sulfoxyethyl methacrylate.

11. The microparticle of claim 1, wherein the pH-sensitive hydrogel is a polyelectrolyte copolymer based on n-methylmethacrylate ester and (dimethylamino)ethyl methacrylate, at a comonomer ratio of 70:30.

12. The microparticle of claim 1, wherein the compound to be delivered to the interior of the cell is a polynucleotide.

13. The microparticle of claim 2, wherein the compound to be delivered to the interior of the cell is a polynucleotide.

14. The microparticle of claim 3, wherein the compound to be delivered to the interior of the cell is a polynucleotide.

15. The microparticle of claim 4, wherein the compound to be delivered to the interior of the cell is a polynucleotide.

16. The microparticle of claim 5, wherein the compound to be delivered to the interior of the cell is a polynucleotide.

17. The microparticle of claim 6, wherein the compound to be delivered to the interior of the cell is a polynucleotide.

18. The microparticle of claim 7, wherein the compound to be delivered to the interior of the cell is a polynucleotide.

19. The microparticle of claim 8, wherein the compound to be delivered to the interior of the cell is a polynucleotide.

20. The microparticle of claim 9, wherein the compound to be delivered to the interior of the cell is a polynucleotide.

21. The microparticle of claim 10, wherein the compound to be delivered to the interior of the cell is a polynucleotide.

22. The microparticle of claim 11, wherein the compound to be delivered to the interior of the cell is a polynucleotide.

23. A composition comprising the microparticle of claim 1 and a buffering agent.

24. A method for delivering a compound to the interior of a cell, comprising introducing a microparticle containing the compound into the endocytic pathway of the cell, wherein the microparticle comprises a pH-sensitive hydrogel in a collapsed state prior to its introduction into the endocytic pathway, but which assumes an expanded state within the endocytic pathway, thereby delivering the compound into the interior of the cell.

25. The method of claim 24, wherein the microparticle comprising the pH-sensitive hydrogel in the expanded state has a diameter which is between five and ten times greater than the diameter of the microparticle comprising the pH-sensitive hydrogel in the collapsed state.

26. The method of claim 24, wherein the microparticle comprising the pH-sensitive hydrogel in the expanded state has a diameter which is between ten and one hundred times greater than the diameter of the microparticle comprising the pH-sensitive hydrogel in the collapsed state.

27. The method of claim 24, wherein the microparticle comprising the pH-sensitive hydrogel in the expanded state has a diameter which is more than one hundred times greater than the diameter of the microparticle comprising the pH-sensitive hydrogel in the collapsed state.

28. The method of claim 24, wherein the pH-sensitive hydrogel expands at a pH of 5.5–6.3.

29. The method of claim 24, wherein the pH-sensitive hydrogel expands at a pH of 5.0–5.5.

30. The method of claim 24, wherein the pH-sensitive hydrogel expands at a pH of less than 5.0.

31. The method of claim 24, wherein the microparticle comprising the pH-sensitive hydrogel in the collapsed state has a diameter of 20–150 nm.

32. The method of claim 24, wherein the pH-sensitive hydrogel comprises a basic monomer unit selected from the group consisting of aminoethyl methacrylate, N,N-dimethylaminoethyl methacrylate, N,N-diethylaminoethyl methacrylate, a moiety comprising imidazole, a moiety comprising an imidazole derivative, vinylpyridine, and vinylbenzyl trimethylammonium chloride.

33. The method of claim 24, wherein the pH-sensitive hydrogel comprises a basic monomer unit and an acidic monomer unit selected from the group consisting of acrylic acid, methacrylic acid, methyl methacrylate ester, sodium styrenesulfonate and sulfoxyethyl methacrylate.

34. The method of claim 24, wherein the pH-sensitive hydrogel is a polyelectrolyte copolymer based on n-methylmethacrylate ester and (dimethylamino)ethyl methacrylate, at a comonomer ratio of 70:30.

35. The method of claim 24, wherein the compound to be delivered to the interior of the cell is a polynucleotide.

36. The method of claim 25, wherein the compound to be delivered to the interior of the cell is a polynucleotide.

37. The method of claim 26, wherein the compound to be delivered to the interior of the cell is a polynucleotide.

38. The method of claim 27, wherein the compound to be delivered to the interior of the cell is a polynucleotide.

39. The method of claim 28, wherein the compound to be delivered to the interior of the cell is a polynucleotide.

40. The method of claim 29, wherein the compound to be delivered to the interior of the cell is a polynucleotide.

41. The method of claim 30, wherein the compound to be delivered to the interior of the cell is a polynucleotide.

42. The method of claim 31, wherein the compound to be delivered to the interior of the cell is a polynucleotide.

43. The method of claim 32, wherein the compound to be delivered to the interior of the cell is a polynucleotide.

44. The method of claim 33, wherein the compound to be delivered to the interior of the cell is a polynucleotide.

45. The method of claim 34, wherein the compound to be delivered to the interior of the cell is a polynucleotide.

* * * * *